United States Patent [19]

Gersten et al.

[11] Patent Number: 5,009,498
[45] Date of Patent: Apr. 23, 1991

[54] INTERCHANGEABLE KERATOSCOPE DEVICE

[75] Inventors: Martin Gersten, Brooklyn; Lars Tibbling, New York; Roy Maus, Brooklyn, all of N.Y.

[73] Assignee: Computed Anatomy Inc., New York, N.Y.

[21] Appl. No.: 496,016

[22] Filed: Mar. 20, 1990

[51] Int. Cl.⁵ .............................................. A61B 3/10
[52] U.S. Cl. ..................................... 351/212; 351/206
[58] Field of Search ................. 351/212, 221, 208, 206

[56] References Cited

U.S. PATENT DOCUMENTS 4,772,115 9/1988 Gersten et al. ..................... 351/212

Primary Examiner—Paul M. Dzierzynski

[57] ABSTRACT

A keratoscopic instrument capable of automatically compensating for the different optical characteristics exhibited by any of a set of mechanically interchangeable illuminated ring devices without manual recalibration includes on the base portion of each light ring device a plurality of distinctive, light pervious, machine-readable indicator spots illuminated from the keratoscope light source and arranged in a code indicative of the optical characteristics of the ring device in place. Marking information is detected and communicated to a computer controlled image processing system wherein the detected information is automatically utilized, in conjunction with other input data, to process the image.

7 Claims, 2 Drawing Sheets

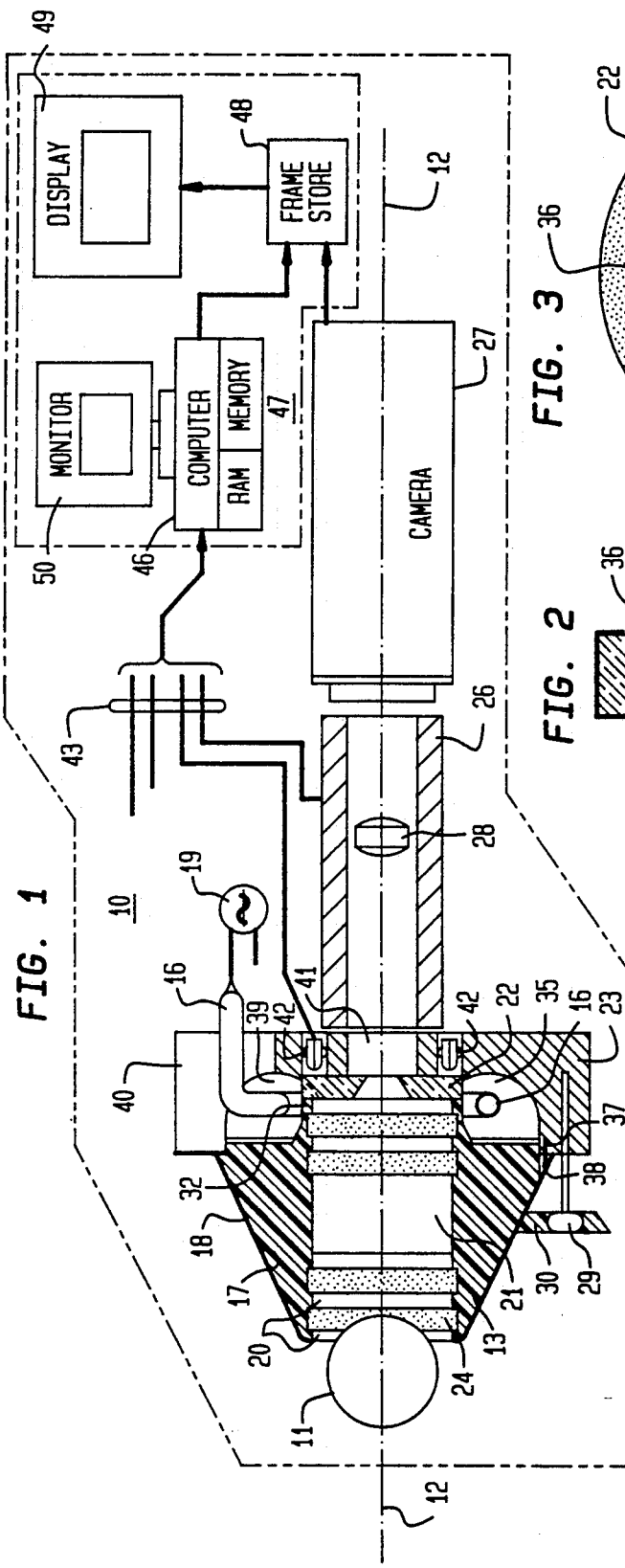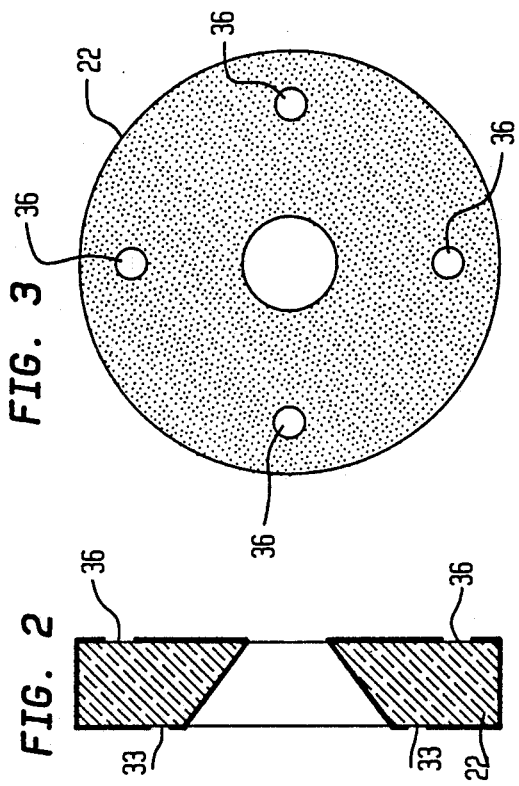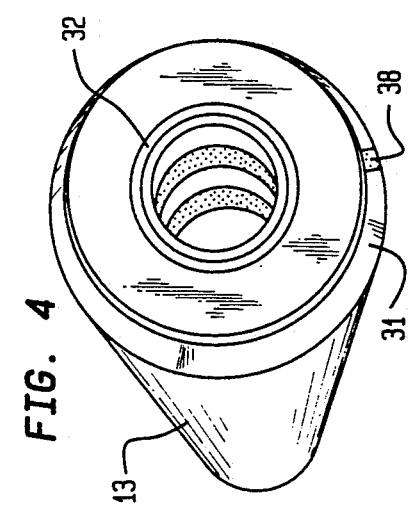

INTERCHANGEABLE KERATOSCOPE DEVICE

TECHNICAL FIELD

This invention relates to instruments, such as keratoscopes, for projecting light rings onto a reflective surface, such as the cornea of the human eye, as an aid in examining its topography.

BACKGROUND ART

One example of such a keratoscope is to be found in the U.S. Pat. No. 4,772,115 to Martin Gersten, Richard J. Mammone, and Joseph Zelvin. In that patent a translucent conical illuminated ring device has a cylindrical bore or passage from its base to its tip lined with set of alternate transparent and opaque rings along the inside surface of the passage. Light from a light box at the base of the cone floods the interior of the cone's material, thereby "back-lighting" the transparent rings. When a curved reflective surface, e.g. the cornea of a patient's eye, is positioned at one end of the passage, an observer, or properly focused camera, looking into the bore's opposite end can acquire an image of the ring pattern appearing on, i.e., reflected from, the object. Variations in the radius of the rings in the pattern from circularity represent distortions of the curved surface.

It has been found to be desirable to be able to use illuminated ring devices having different diameter rings to accommodate the variation in human physiology and to produce different patterns of illumination that may appropriate for examining patients with different eye maladies. However, the computer controlled machine described in the above-mentioned patent is calibrated for use with a particular illuminated ring device having a predetermined diameter and pattern of rings. Substitution of a different device would require time-consuming re-calibration or re-programming of the machine for each different arrangement of light ring device employed.

DISCLOSURE OF INVENTION

In accordance with the principles of the present invention the illuminated ring light devices for use in a computer-controlled keratoscope system are made interchangeable so that light ring devices with different patterns or other optical characteristics can be used without requiring manual recalibration. Each light ring device includes a plurality of distinctive, light pervious, machine-readable indicator spots illuminated from the keratoscope light source and arranged in a code indicative of the calibration characteristics of the light ring device. The light ring devices engage a socket on the apparatus which includes an array of photodetectors that are energized by the illuminated spots to indicate to the computer system a binary coded combination that identifies a particular type of light ring device.

BRIEF DESCRIPTION OF DRAWINGS

A more complete understanding of various features, objects, and advantages of the invention can be obtained from a consideration of the following description and the appended claims in connection with the attached drawings in which:

FIG. 1 is a cross-sectional view of selected portions of a keratoscope including the invention;

FIG. 2 is an enlarged cross-sectional view of an aperture disk portion of a light ring device in the keratoscope of FIG. 1;

FIG. 3 is a side view of the aperture disk of FIG. 2;

FIG. 4 is a base-end, bottom, left perspective view of the light ring device of FIG. 1;

BEST MODE FOR CARRYING OUT THE INVENTION

Figure 5:
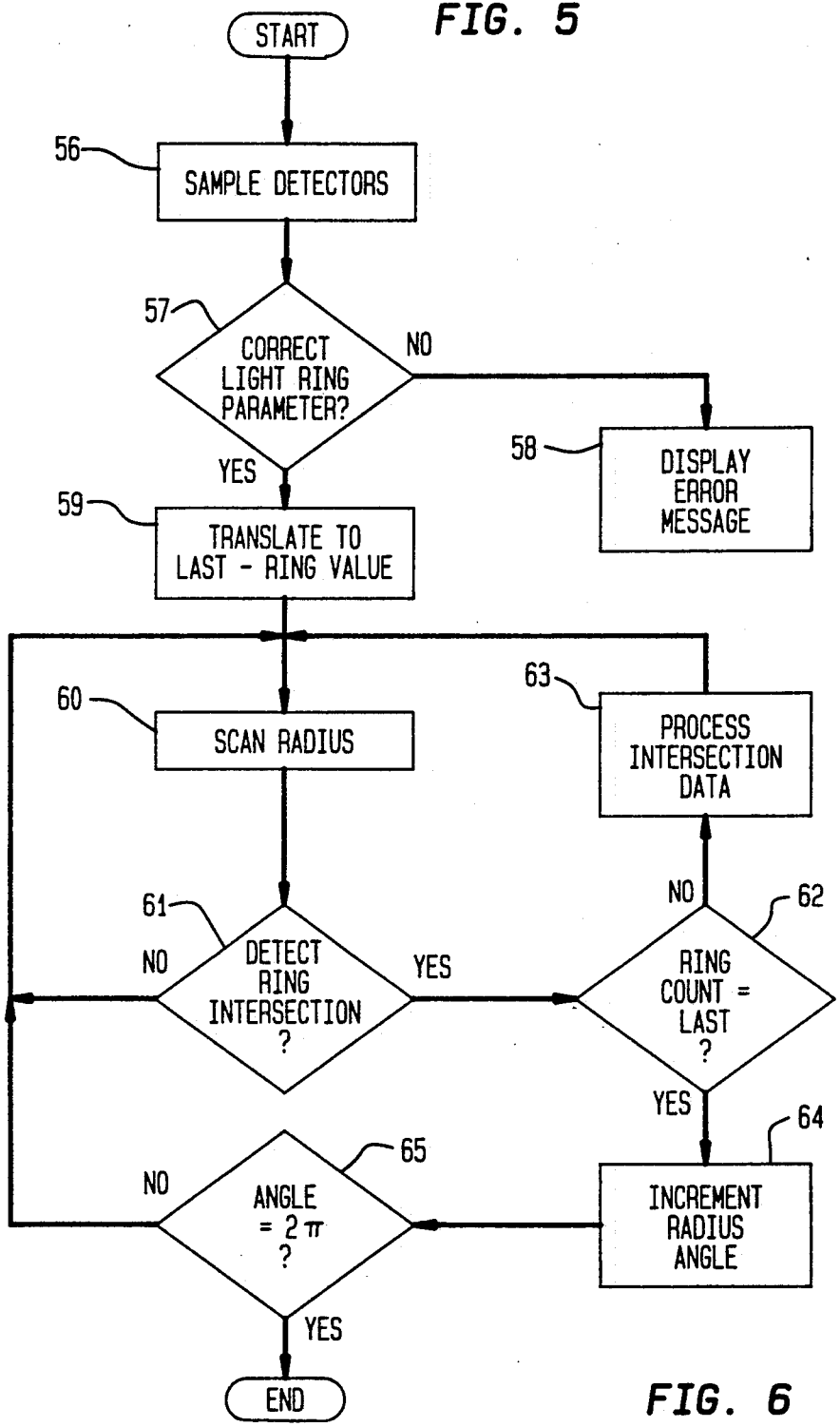
FIG. 5 is a process flow diagram illustrating the use of an indicator named light ring device parameter in the program of the keratoscope of FIG. 1.

In FIG. 1 there are shown in schematic form, and partly in central cross section taken along an optical axis, several elements of a keratoscope 10, for examining a light-reflective curved surface such as the surface of the cornea of a human eye. More detailed background information about such a keratoscope, may be found in, for example, the aforementioned M. Gersten et al. patent and in the copending U.S.A. patent application of M. Gersten, R. Maus, and L. Tibbling, Ser. No. 07/492,939, filed 3/13/1990, entitled "Illuminated Ring Device," and assigned to the same assignee as the present application. Both that Gersten et al. instrument and the present illustrative embodiment employ a conical light ring device 13 of a light pervious material such as transparent plexiglass having a longitudinal, cylindrical passageway or bore 21 adapted to have its translucent rings 20 spaced along the interior of a cylindrical passage 21 receive illumination from a light box 23. As disclosed in the above-mentioned co-pending application, light box 23 includes an annular reflective concavity 39 to accommodate toroidal fluorescent tube 16. Three bodies 35 of adhesive bonding material, only one of which appears in FIG. 1, are located at approximately equally space points around the circular part of tube 16 between the tube and reflective surface 39 of light box 23 to support tube 16 in its position shown within light box 23. One suitable bonding material is commercially available silicone glue.

As can be seen in FIG. 1, the concavity of the surface 39 is approximately circular in cross section; and the circular portion of toroidal tube 16 is advantageously located with its toroidal loop center line approximately coincident with a circle including the centers for arcs of circles comprising that circular cross section. Thus, a substantial part of the light emitted from tube 16 in directions other than toward ring device 13 or disk 22 is intercepted by the reflective surface 28 and redirected thereby back toward the base of ring device 13 in an approximately collimated fashion.

Light from tube 16 enters the translucent base of conical portion 13 and illuminates translucent rings 20. Rings 20 are advantageously defined by the uncoated minor diameters of bore 21, the major diameters being provided with an opaque coating to define rings 24. Passage 21 is coaxial with the visual axis 12.

The image of rings 20 appearing on the surface of target 11 is reflected, with such distortions as are caused by defects in its reflective surface, back along the passage 21 through central apertures in a disk 22 and light box 23, both coaxial with the visual axis 12, and is acquired by camera 27 via lens 28 mounted in extension tube 26.

Cone 13 is mounted to light box 23 via thumb screws 29, one being shown in FIG. 1, each having a resilient rim portion 30, frictionally engage exterior surface 18 of cone 13. When the screws are threaded into the body of light box 23, they hold the ring device in place with a shoulder 31 (best seen in FIG. 4), on the outer extremity of the base of the ring device, against light box 23. Light box 23 is adapted to receive any of a plurality of mechanically interchangeable set of light ring device cones 13 by loosening at least one of the screws 29, lifting out the ring device and inserting a different ring device, and replacing the thumb screws. A key 37 secured in the lower portion of the body of light box 23 engages a keyway 38, seen most clearly in FIG. 4, in the rim of ring device 13 conical base region permits only a single orientation of ring device 13 in light box 23. Thus, cone light ring devices having different numbers of rings and hence different lengths, but the same right-hand shoulder and keyway configuration will be mechanically interchangeably mountable to light box 23.

Disk 22 of translucent material is secured to the right-hand end of extension 32, e.g. by a bonding material such as epoxy glue, and is a toroid of trapezoidal cross section with its interior edge beveled to face the eye 11. An outer diameter of the disk is approximately the same as that of the extension 32; and an inner diameter, the aperture of the optical system, is sufficient to pass focused light of the reflected image from eye 11.

Disk 22, shown in enlarged cross section in FIG. 2., is provided with an opaque coating similar to that defining opaque rings 24. The opaque coating of its face closest to target 11 is relieved to provide an illuminated ring 33. In addition a portion of the interior beveled face of disk 22 may also be relieved to define a circular ring (not shown). Light from fluorescent tube 16 enters the outer circumference of disk 22 to illuminate the ring 33 by back lighting.

In FIG. 1 cone 13 is provided with a bore 21 of given diameter having a given arrangement of illuminated rings 21 (disc 22 has a given type of ring 33). It may be advantageous under certain circumstances, however, to use a cone having a different bore diameter and different pattern of rings. This requires that the image acquisition system comprising camera 27 and computer 46 be re-calibrated to provide the appropriate scanning of the image as the rings appearing on target 11 will be located in a different position.

In order to distinguish automatically among the mechanically interchangeable light ring devices of different types which produce these different optical effects, a distinctive, multistate, machine readable indicator is applied to each ring device. The term "machine readable" is here employed to include indicators that are readable by electrical, optical, mechanical, or other nonhuman means, whether or not such machine readable means are also humanly readable. Optical indicators are presently preferred, and one example is illustrated here.

In accordance with this aspect of our invention, an opaque coating over a reflective white undercoating is also applied to most of the right-hand (as illustrated) face of disk 22 remote from target 11. A plurality of coding spots 36 are allocated on that right-hand face, and arranged according to a predetermined coding rule, for indicating one or more characteristics of the ring device 13 to which the disk is secured. Four such spots are shown in the drawing, and all are for convenience of illustration shown as having no coating on them; so they will be illuminated from the interior of the disk by light from tube 16. Each spot may be either coated or uncoated to provide, in combination, a coded representation of predetermined characteristics or other values unique to each ring device 13. For example, it is presently preferred to use the spots to indicate in a binary coding system different types of ring device 13, each type having a different number of illuminated rings 20 in its passage 21. According to binary theory, four such spots are sufficient to define 16 different types of cones according to whether none, one, two, three, or all four spots are uncoated.

A central opening 41 through light box 23 is defined at the inner edge of surface 39 by a substantially recessed circular seat against which the ring device 13 with its attached disk 22 is assembled. Opening 41 is coaxial with visual axis 12. A plurality of photodiode detectors 42, sometimes herein called photodetectors, are mounted in holes in the body of light box 23. Four such detectors are provided, as schematically represented by the four coupling circuits 43 extending to an input/output connection of a microcomputer 46 of a computer controlled display subsystem 47. Each detector is immediately opposite one of the binary coded spots 36 on the back side of disk 22 and sufficiently close to that spot to be able to detect whether or not the spot is uncoated when the disk interior is illuminated. Edges of disk 22 block significant light leakage from the concave side of light box 23 to the photodetectors 42.

In display subsystem 47, a frame store 48 and the microcomputer 46 are provided for acquiring, storing, and processing a two-dimensional image of the illuminated rings 20 reflected from eye 11. Microcomputer 46 includes random access memory and bulk memory as shown in the drawing. A video monitor 49 displays an image coupled from camera 24 via frame store 48 in either the form initially acquired by the camera 27 or a form which has been enhanced by the computer processing as is now known in the art. A computer monitor 50 displays the menu for guiding a keratoscope operator through the processing steps.

Figure 6:
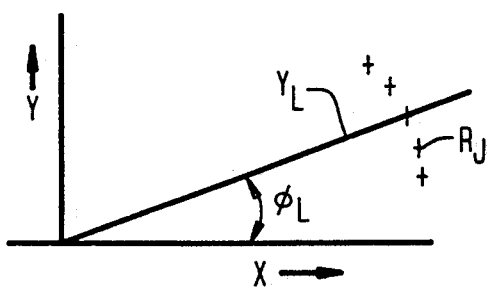
FIG. 6 is a diagram of image data scanning parameters used in FIG. 5.

FIG. 5 is a process flow diagram illustrating one way to incorporate the use of coded spots 36 into one well-known radial scanning routine for keratoscopic image data processing. Reference characters in parentheses correspond to similarly designated steps in FIG. 5. FIG. 6 is a diagram to facilitate consideration of FIG. 5 and shows an arbitrary radius ri extending from a center point at the X-Y axis origin, at an arbitrary angle $\phi i$ with respect to the X-axis. That center point represents a central point in an image. Image data points for a last-ring Ri are also shown.

At the start of the FIG. 5 process, outputs of detectors 42 are sampled (56) and tested (57) against user-provided initializing input data stored in the memory of microcomputer 46 to determine whether or not the proper type of ring device 13 is in place. If it is not, an error message is displayed (58); and the process is interrupted until corrective action is taken. If the proper ring device type is in place, the value represented by the binary coded, detector states information is translated (59) to obtain a last-ring count value for the particular application involved and which count will be used to limit the extent of scanning along different radii from a predetermined display center point to locate intersections with reflected images of illuminated rings 20.

An initial radium scan is begun (60). At successive points along the radius ri, image picture element intensity values are compared to detect (61) intersections with reflections of bright illuminated rings 20. If no intersection is detected the test location is incremented out along the radius to make a new test. If an intersection is detected, a count of intersections found so far in the scan is compared (62) to the last-ring count from step (59). If the last-ring Ri has not been reached, the intersection data is processed (63); and the scan location is incremented again. If the last ring has been reached, the radius angle $\phi i$ is incremented (64) and the new angle checked (65) to see whether or not a full circular scan has been completed. If it has, the process ends; but if it has not, a scan from center at the new radius angle is begun (60).

Although the invention has been illustrated in terms of one particular embodiment, modifications which will be apparent to those skilled in the art are included within the spirit and scope of the invention.

What is claimed is:

1. A keratoscope image processing system comprising a light box and a conical body of translucent material having a cylindrical bore defining a series of light transmitting rings, the improvement wherein said conical body includes a plurality of light-pervious machine readable spots disposed to receive a portion of said light from said light box, said machine readable spots being arranged in a binary pattern indicative of the optical characteristics of said conical body, means for storing image processing initializing data including signal values representing predetermined types of illuminated ring light ring devices, and means responsive to said binary pattern and said signal values for modifying said processing of said keratoscope image.

2. The keratoscope image processing system of claim 1 wherein a plurality of light-sensing diodes is disposed in said light box to monitor the light transmitted through said light pervious spots and means for coupling an output of said diodes to said processing means, said processing means being responsive to said output to compensate for the optical characteristics identified by said pattern.

3. The keratoscope image processing system of claim 1 wherein said light box includes a reflective concavity, a fluorescent tube disposed in said concavity to direct light into said base portion of said conical body, a disc having said light pervious spots being disposed in said bore to receive a portion of the light introduced into said concavity.

4. The keratoscope image processing system of claim 3 wherein said disc includes an opaque coating on its faces, said coating being removed on one face to reveal a light-transmitting ring facing said target and being removed on an opposite face away from said target to reveal said machine-readable spots.

5. An illuminated ring device for use in a keratoscope image processing system comprising a light box and a conical body of translucent material having a cylindrical bore defining a series of light transmitting rings, the improvement wherein said light box includes a shoulder recess for receiving the base portion of said conical body, said conical body having a disc of translucent material disposed in said bore providing plurality of light-pervious machine readable spots to receive a portion of said light from said light box, said spots being arranged in a binary pattern indicative of the optical characteristics of said conical body, said conical body including a keyway and said lightbox including a mating key for maintaining said conical body in alignment with said lightbox, a plurality of light-sensing diodes disposed to monitor the light transmitted through said light pervious spots of said disc and means for coupling an output of said diodes to said processing means, said processing means being responsive to said output to compensate for the optical characteristics identified by said pattern.

6. The illuminated ring device of claim 5 wherein means said light box includes a reflective concavity, a fluorescent tube disposed in said concavity to direct light into said base portion of said conical body, said disc being disposed to receive a portion of the light introduced into said concavity.

7. The illuminated ring device of claim 5 wherein said disc includes an opaque coating on its faces, said coating being removed on one face to reveal a light-transmitting ring facing said target and being removed on an opposite face away from said target to reveal said machine-readable spots.

* * * * *